United States Patent [19]
Allen et al.

[11] Patent Number: 5,804,562
[45] Date of Patent: Sep. 8, 1998

[54] SPIROSTANYL GLYCOSIDAL CRYSTALS

[75] Inventors: Douglas John Allen; Richard A. Buzon, both of New London; Michael P. Deninno, Gales Ferry; Harry Austin Watson, Jr., Groton; Jonathan B. Zung, East Lyme, all of Conn.

[73] Assignee: Pfizer Inc., New York, N.Y.

[21] Appl. No.: 809,160

[22] Filed: May 1, 1997

Related U.S. Application Data

[63] Continuation of Ser. No. 298,106, Aug. 30, 1994, abandoned.

[51] Int. Cl.⁶ .......................... A61K 31/705; C07J 21/00
[52] U.S. Cl. .................................. 514/26; 514/824; 536/5
[58] Field of Search ........................... 514/26, 824; 536/5

[56] References Cited

U.S. PATENT DOCUMENTS 5,698,526 12/1997 Deninno ..................................... 514/26

FOREIGN PATENT DOCUMENTS

WO9518144 7/1995 WIPO .

*Primary Examiner*—Kathleen K. Fonda
*Attorney, Agent, or Firm*—Peter C. Richardson; Gregg C. Benson; A. Dean Olson

[57] ABSTRACT

Crystalline spirostanyl glycosides and processes for making them are disclosed. The crystalline spirostanyl glycosides are useful for treatment of hypercholesterolemia or atherosclerosis.

11 Claims, 2 Drawing Sheets

SPIROSTANYL GLYCOSIDAL CRYSTALS

BACKGROUND OF THE INVENTION

This application was filed under 35 U.S.C. §371 based on PCT/IB95/00317, which was filed on May 4, 1995 which is a continuation of U.S. application Ser. No. 08/298,106 which was filed on Aug. 30, 1994 and is now abandoned.

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives, such as of polystyrene. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficacy. Thus, the effective hypocholesterolemic dose of these materials is excessive, typically 18–24 grams of ormulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of nonuseful chemical substances. Due to the variations in composition, it is difficult to set a standard dosage or predict the impurities present. Thus, such extracts are not well suited for use by humans. Further, purification of these extracts would be expensive. As an alternative, certain synthetically produced, pure "sapogenin-derived" compounds, e.g., substances compounded from spirostane, spirostene or sterol-derived compounds, depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive amounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, lu. K. Vasilenko, G. M. Gorianu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyrarnine.

Also, other steroidal glycosides (e.g., (3β,5α,25R)-3-[(β-D-cellobiosyl)oxy]spirostan-12-one) having superior hypocholesterolemic activity are disclosed in commonly assigned PCT application PCT/US93/04092 published as WO 94/00480 (the disclosure of which is hereby incorporated by reference) and in commonly assigned U.S. patent application Ser. No. 08/054,449 filed Apr. 28, 1993 (now PCT/US/00446) the crystalline monohydrate of (3β,5α,25R)-3-[(β-D-cellobiosyl)oxy]spirostan-11-one and it's use as a hypocholesterolemic agent and antiatheroscelerosis agent is disclosed.

In addition, commonly assigned U.S. patent application Ser. Nos. 08/174,100 now abandoned, and 08/174,099 now abandoned (the disclosures of which are hereby incorporated by reference) disclose additional steroidal glycosides (e.g., (3β,5α,25R)-3-[(β-D-4",6"-bis-[2-fluorophenylcarbamoyl] cellobiosyl)oxy]-spirostan-12-one) having superior hypocholesterolemic activity.

Thus, although there are a variety of hypercholesterolemia controlling agents there is a continuing search in this field of art for alternative agents.

SUMMARY OF THE INVENTION

One aspect of this invention is directed to two highly crystalline forms (hereinafter denoted form A and form B) of a spirostanyl glycoside that are useful as hypocholesterolemic or antiatheroscierosis agents. The compound is (3β, 5α,25R)-3-[(β-D-4",6"-bis-[2-fluorophenylcarbamoyl] cellobiosyl)oxy]-spirostan-12-one) and has the following X-ray diffraction d-spacing:

| Form A d-spacing of 20 largest peaks | or | Form B d-spacing of 12 largest peaks |
|---|---|---|
| 21.10 | | 19.96 |
| 17.46 | | 17.11 |
| 13.58 | | 15.14 |
| 10.49 | | 9.97 |
| 6.98 | | 7.57 |
| 6.78 | | 6.62 |
| 6.60 | | 6.09 |
| 6.34 | | 5.36 |
| 5.77 | | 5.15 |
| 5.52 | | 4.90 |
| 5.35 | | 4.57 |
| 5.12 | | 3.77 |
| 4.82 | | |
| 4.53 | | |
| 4.37 | | |
| 4.12 | | |
| 3.82 | | |
| 3.55 | | |
| 3.44 | | |
| 3.37. | | |

The crystalline form A spirostanyl glycoside is preferred and has the following d-spacing:

| Form A d-spacing of 20 largest peaks |
|---|
| 21.10 |
| 17.46 |
| 13.58 |
| 10.49 |
| 6.98 |
| 6.78 |
| 6.60 |
| 6.34 |
| 5.77 |
| 5.52 |
| 5.35 |
| 5.12 |
| 4.82 |
| 4.53 |
| 4.37 |
| 4.12 |
| 3.82 |
| 3.55 |
| 3.44 |
| 3.37 |

The Crystalline form B spirostanyl glycoside is another aspect of this invention and has the following d-spacing:

| Form B d-spacing of 12 largest peaks |
| --- |
| 19.96 |
| 17.11 |
| 15.14 |
| 9.97 |
| 7.57 |
| 6.62 |
| 6.09 |
| 5.36 |
| 5.15 |
| 4.90 |
| 4.57 |
| 3.77 |

Yet another aspect of this invention is directed to pharmaceutical compositions for the treatment of hypercholesterolemia or atherosclerosis in mammals which comprise a crystalline compound as described above and a pharmaceutically acceptable carrier.

Yet another aspect of this invention is directed to a method for treating hypercholesterolemia or atherosclerosis in a mammal by administering to a mammal suffering from hypercholesterolemia or atherosclerosis a therapeutically effective amount of a crystalline compound as described above.

Yet another aspect of this invention is directed to a process for preparing a crystalline compound as described above. The process comprises crystallization from a suitable solvent, preferably ethyl acetate or acetonitrile. In a preferred aspect of this process (3β,5α,25R)-3-[(β-D-4",6"-bis-[2fluorophenylcarbamoyl]cellobiosyl)oxy]-spirostan-12-one is mixed in sufficient ethyl acetate or acetonitrile for a sufficient time to provide, upon cooling, crystalline (3β,5α,25R)-3-[(β-D-4",6"-bis-[2-fluorophenylcarbamoyl]cellobiosyl)oxy]-spirostan-12-one.

Thus this invention makes a significant advance in the art by providing a first (form A) nonhygroscopic, thermodynamically stable, highly crystalline form of (3β,5α,25R)-3-[(β-D-4",6"-bis-[2-fluorophenylcarbamoyl]cellobiosyl)oxy]-spirostan-12-one) and a second (form B) crystalline form of the named compound that is more thermodynamically stable than a third, previous crystalline form of the named compound. These crystals facilitate the development and regulatory review of the compound. In addition, the preferred crystalline form of this invention has superior handling and formulation (e.g., tabletting) characteristics due to its nonhygroscopic nature. In comparison, a third previous form of the compound is microcrystalline with no discernible habit. This latter form is less thermodynamically stable, as it is crystalline with an element of disorder, and has a waxy consistency (due to its hygroscopic nature) that makes it extremely difficult to filter, handle and formulate.

Other features and advantages will be apparent from the specification and claims and from the accompanying drawings which illustrates embodiments of the invention.

DETAILED DESCRIPTION OF THE INVENTION (3β,5α,25R)-3-[(β-D-4",6"-bis-[2-fluorophenylcarbamoyl]cellobiosyl)oxy]-spirostan-12-one) has the formula

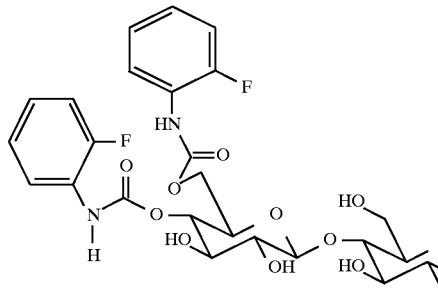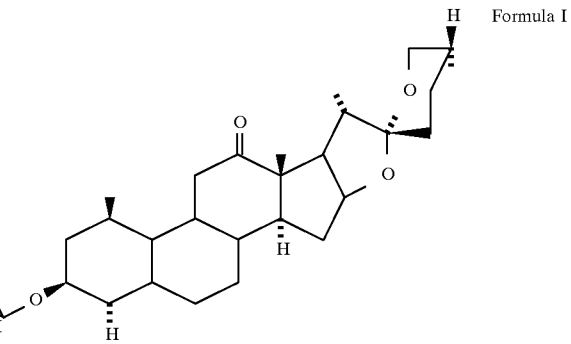

Formula I

The compound of Formula I is herein defined as the single enantiomer having the absolute stereochemistry depicted in Formula I.

Figure 1:
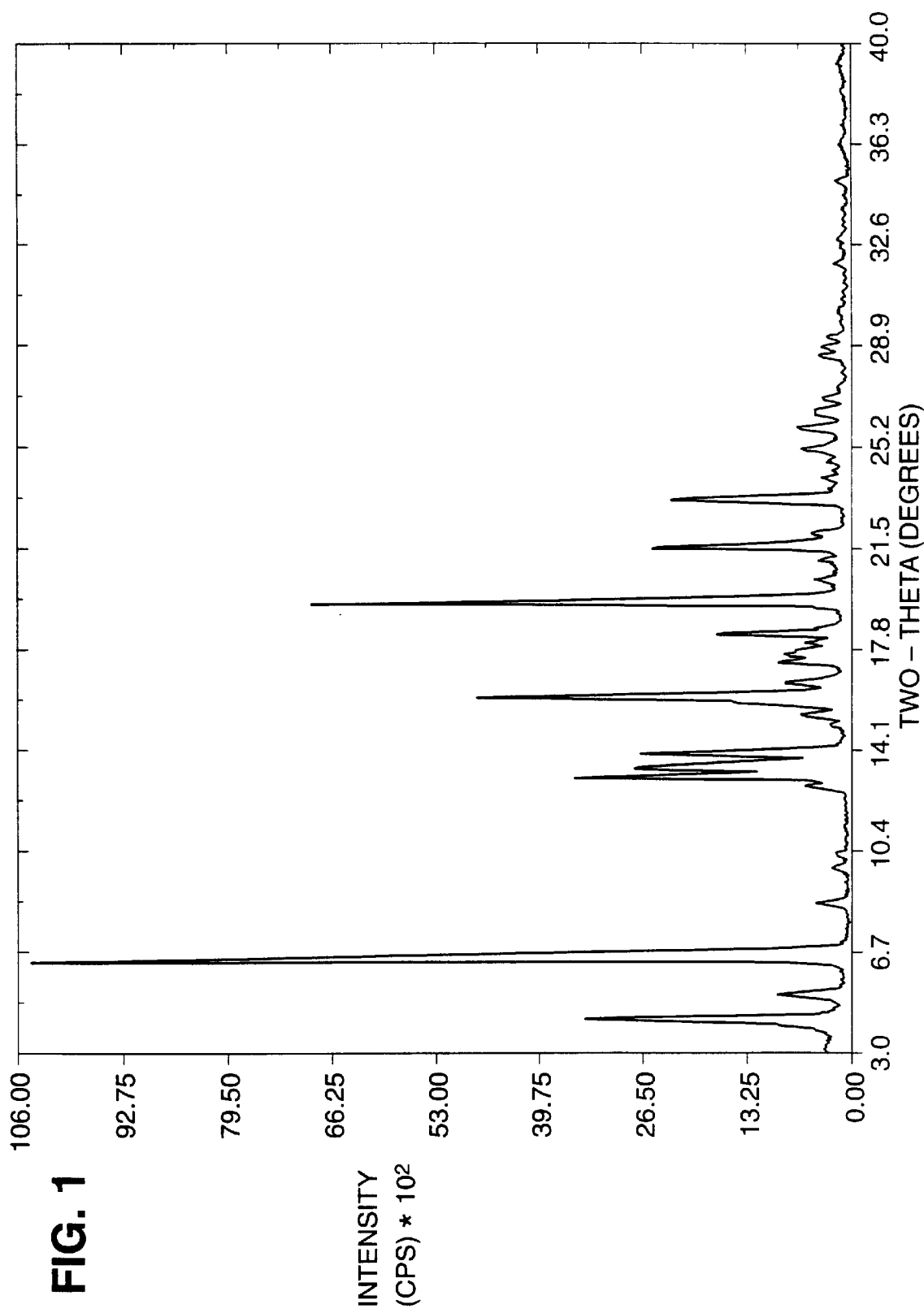
FIG. 1 illustrates an X-ray powder diffraction pattern of the first preferred crystal form A of this invention.

According to this invention there are two highly crystalline forms of the compound of Formula I. An understanding of this invention may be had by reference to FIGS. 1 (form A) and 2 (form B) which illustrate X-ray powder diffraction patterns of the highly crystalline forms of this invention. In both figures, intensity (Y) in cps is graphed against two theta (X) in degrees. These X-ray powder diffractions were taken with a Siemens diffractometer Model 5000 (Madison, Wis.) under ambient conditions.

Both of the crystalline forms A and B are doubly terminated blades in habit. The preferred form A has been observed as a mixture of rod or doubly terminated blades, however, it is believed the rod is an interim habit and the blade is the ultimate habit. Because form A exists in both crystalline habits yet still has the same crystalline lattice it is believed that either habit could be isolated exclusively. The preferred form A is nonhygroscopic. Form B exists in hydrated or solvated forms. In addition, both crystalline forms have been observed as thin flake.

A preferred highly crystalline form A of the above described compound may be prepared according to the following procedure. Substantially pure (less than about 10% impurities, excluding residual solvents such as water) amorphous or crystalline (3β,5α,25R)-3-[(β-D-4",6"-bis-[2-fluorophenylcarbamoyl]cellobiosyl)oxy]-spirostan-12-one) is converted to a first highly crystalline form A by mixing (e.g., dissolving, slurrying) the amorphous or crystalline material in a suitable solvent (although clearly the conversion to the desired crystalline phase involves the dissolution of either the amorphous or crystalline material and precipitation of the desired crystalline form), preferably ethyl acetate or acetonitrile, followed by (re)crystallization.

Preferably, the concentration of compound to solvent is about 1:100 to about 1:1 by weight/volume. It is especially preferred that the concentration is from about 5:100 to about 20:100.

Preferably, the dissolution temperature varies from ambient (e.g., 17° C. to 300° C.) to reflux, with temperatures of 60° C. to reflux being more efficient. Typically the elevated temperatures are maintained for about one-half hour to 24 hours. If elevated temperatures are used for dissolution the resulting suspension is allowed to cool to ambient temperature and the crystals are granulated for about one-half hour to 60 hours and then collected by conventional means, preferably filtration and vacuum drying.

Alternatively, the starting material may be dissolved in a first solvent such as ($C_1$–$C_6$)alkylketones, THF/ cyclohexane, ($C_1$–$C_4$)alkanols or chlorinated hydrocarbons such as methylene chloride, preferably tetrahydrofuran/ cyclohexane 3:1, followed by (re)crystallization upon exposure to ethyl acetate or acetonitrile (e.g., displacement of the first solvent with the second during distillation).

Another highly crystalline form B of the above described compound may be prepared in an analogous manner according to the above procedures (including the alternative procedure in the preceding paragraph) except using an alkanol ($C_1$–$C_4$) optionally with up to 70% water, such as ethanol, isopropanol or n-propanol(30 to 70%)/water(70 to 30%), as the recrystallization solvent.

(3β,5α,25R)-3-[(β-D-4",6"-bis-[2-fluorophenylcarbamoyl]cellobiosyl)oxy]-spirostan-12-one) is prepared according to the methods disclosed in commonly assigned U.S. patent application Ser. No. 08/174,100 filed Dec.28, 1993, now abandoned (the disclosure of which is hereby incorporated by reference).

In particular, the claimed compound may be prepared as follows:

(3β,5α,25R)-3-[(β-D-4",6"-bis-[2-fluorophenylcarbamoyl cellobiosyl]-2',2",3',3",6'-penta-chloroacetyl-cellobiosyl)oxy]-spirostan-12-one is deacetylated by combination with a nucleophilic base such as sodium methoxide or potassium cyanide in a polar solvent such as methanol, tetrahydrofuran, n-propanol or mixtures thereof at temperatures of about 0° C. to about 100° C. (typically at ambient temperatures) and pressures of about 0.5 psi to about 50 psi (typically ambient) for about 0.25 hour to about 2 hours (typically 0.5 hour) to give (3β,5α, 25R)-3-[(β-D-4",6"-bis-[2-fluorophenylcarbamoyl] cellobiosyl)oxy]-spirostan-12-one). (3β,5α,25R)-3-[(β-D-2',2",3',3",6'-penta-chloroacetyl-cellobiosyl)oxy]-spirostan-12-one is converted to the carbamoyl moiety by combination with the appropriate isocyanate (i.e., 2-fluorophenylisocyanate) in the presence of cuprous chloride in a polar aprotic solvent such as dimethyl formamide at ambient temperature for two hours to about 10 hours to produce (3β,5α,25R)-3-[(β-D-4",6"-bis-[2-fluorophenylcarbamoyl cellobiosyl]-2',2",3',3",6'-penta-chloroacetyl-cellobiosyl)oxy]-spirostan-12-one.

[(β-D-4",6"-O-[4-methoxybenzylidene]-2',2",3',3",6'-penta-chloro-acetylcellobiosyl)oxy]-spirostan-12-one is treated with trifluoroacetic acid in a mixture of dichloromethane and methanol at ambient temperature for about two hours to about eight hours to prepare (3β, 5α,25R)-3-[(β-D-2',2",3',3",6'-penta-chloroacetylcellobiosyl)oxy]-spirostan-12-one.

(3β,5α,25R)-3-[(β-D-cellobiosyl)oxy]-spirostan-12-one is reacted with anisaldehyde dimethyl acetal, in the presence of a catalytic amount of a strong acid such as camphorsulfonic acid in an anhydrous, aprotic solvent such as chloroform or dichloroethane under reflux conditions for about two to about six hours at ambient pressure. Upon completion of the ketalization, a base preferably an amine base such as pyridine and an acylating agent such as chloroacetic anhydride are added at a temperature of about −20° C. to about 10° C. followed by ambient temperature stirring for about one to about twelve hours (typically about 2 hours) to prepare (3β, 5α,25R)-3-[(β-D-4",6"-O-[4-methoxybenzylidene]-2',2",3',3",6'-penta-chloro-acetylcellobiosyl)oxy]-spirostan-12-one.

(3β,5α,25R)-3-[(heptaacetyl-β-D-cellobiosyl)oxy] spirostan-12-oneisdeacetylated by combination with a nucleophilic base such as sodium methoxide or potassium cyanide in a solvent such as methanol, tetrahydrofuran, n-propanol or mixtures thereof at elevated temperatures of about 40° C. to 100° C. (typically at reflux) and pressures of 0.5 psi to about 50 psi (typically ambient) for about 0.25 hour to about three hours to give (3β,5α,25R)-3-[(β-D-cellobiosyl)oxy]spirostan-12-one.

(3β,5α,25R)-3-[(heptaacetyl-β-D-cellobiosyl)oxy]-spirostan-12-oneispreparedby coupling heptaacetyl-β-D-cellobiosyl bromide and (3β,5α,25R)-3-hydroxy-spirostan-12-one in a non-protic, anhydrous reaction inert solvent (e.g., acetonitrile) at atemperature of about 20° C. to about 100° C. for about 0.5 to about 12 hours in the presence of 0.5 to about 4 equivalents zinc fluoride.

The starting materials of the above described reactions (e.g., peracetylated sugar halide) are readily available or can be easily synthesized by those skilled in the art using conventional methods of organic chemistry. In particular, (3β,5α,25R)-3-hydroxyspirostan-12-one (i.e., hecogenin) is available from Sigma Chemical Company, St. Louis, Mo. or Steraloids Inc., Wilton, N.H. In addition, its isolation and purification from natural products are described in Rodd's Chemistry of Carbon Compounds, S. Coffey ed., Vol. 11, Part E, pp.1–53, 1971.

The compound of this invention is a potent inhibitor of cholesterol absorption and thus is adapted to therapeutic use as a hypercholesterolemia controlling agent in mammals, particularly humans. Since hypercholesterolemia is closely related to the development of generalized cardiovascular, cerebral vascular or peripheral vascular disorders, secondarily this compound prevents the development of atherosclerosis particularly arteriosclerosis.

The hypercholesterolemia controlling activity of this compound may be demonstrated by methods based on standard procedures. For example, the in vivo activity of this compound in inhibiting intestinal absorption of cholesterol may be determined by the procedure of Melchoir and Harwell (J. Lipid Res., 1985, 26, 306–315).

Activity can be determined by the amount of hypocholesterolemic agent that reduces the cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day the animals are fasted for 18 hours, then administered a 1.5 mL oral bolus of water containing 0.25% methylcellulose, 0.6% Tween 80 and 10% ethanol (control animals) or an oral bolus that contains, in addition, the desired concentration of the compound to be tested. Immediately following bolus administration, the animals receive a second 1.5 mL oral bolus of liquid hamster diet containing 1% [$^3$ H] cholesterol (2.0 μCi/animal; 210 dpm/nmol) and 0.5% cholic acid, and are fasted for an additional 24 hours. At the end of this second fasting period animals are sacrificed livers, are excised, saponified and aliquots are decolorized by addition of hydrogen peroxide, and assessed for radioactivity. Total hepatic radioactivity is calculated based on measured liver weights. The degree of cholesterol absorption is expressed as a percentage of the total radioactivity administered as an oral bolus that is present in the liver 24 hours following bolus administration.

Anti-atherosclerosis effects of the compound (i.e.,activity and thus dosages) can be determined by the amount of agent of this invention that reduces the lipid deposition, relative to the control, in the aorta of male New Zealand white rabbits. Male New Zealand white rabbits are fed a diet containing 0.4% cholesterol and 5% peanut oil for 1 week (meal-fed once a day). After 1 week some of the rabbits (the control group) continue with the diet and the remainder receive the diet supplemented with the desired concentration of the compound to be tested. After 8.5 weeks, drug treatment is discontinued and the animals are maintained on the cholesterol containing diet for an additional 2 weeks and then switched to a cholesterol free diet for 5 weeks. The animals are sacrificed, and the aortas removed from the thoracic arch to the branch of the iliacs. The aortas are cleaned of adventitia, opened longitudinally and then stained with Sudan IV as described by Holman et al. (Lab. Invet. 1958, 7, 42–47). The percent of the surface area stained is quantitated by densitometry using an Optimas Image Analyzing System (Image Processing Systems). Reduced lipid deposition is indicated by a reduction in the percent surface area stained in the drug treated group in comparison with the control rabbits.

Administration of the compound of this invention can be via any method which delivers the compound to the intestinal lumen. These methods include oral routes, intraduodenal routes, etc.

The amount of steroidal glycoside administered will, of course, be dependent on the subject being treated, on the severity of the affliction, on the manner of administration and on the judgement of the prescribing physician. However, an effective dosage is in the range of 0.005 to 20 mg/kg/day, preferably 0.01 to 5 mg/kg/day, most preferably 0.01 to 1 mg/kg/day. For an average 70 kg human, this would amount to 0.00035 to 1.4 g/day, preferably 0.0007 to 0.35 g/day, most preferably 0.0007 to 0.07 g/day.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an anti-hypercholesterolemia or anti-atherosclerosis effective amount.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing the steroidal glycoside of this invention, and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see Remington's Pharmaceutical Sciences., Mack Publishing Company, Easter, Pa., 15th Edition (1975).

Example 1

Crystalline (3β,5α,25R)-3-[(β-D-4",6"-Bis[2-fluorophenyl carbamoyl]-cellobiosyl)oxy]-spirostan-12-one (3β,5α,25R)-3-[(β-D-4",6"-Bis[2-fluorophenyl carbamoyl]-cellobiosyl)oxy]-spirostan-12-one (468 g) was recrystallized from THF/cyclohexane (3:1) as described below (see Preparation A1). Subsequent to recrystallization the undried cake was dissolved in 8.4 L of THF at 30° C., filtered and atmospherically distilled (i.e., at ambient pressure) replacing the distillate with ethyl acetate. When a final volume of 12 L had been reached and the distillates had the refractive index of ethyl acetate, the mixture was cooled to 20°–25° C., granulated overnight, filtered and dried to afford 363.3 g of the title compound as a white to off-white solid form A that is thin flake with a mixture of rod and doubly terminated blades habit. A representative X-ray diffraction pattern of this preferred crystal (made substantially as described above) is depicted in FIG. 1.

In an analogous manner the product of Example 1 was prepared by substituting acetonitrile for ethyl acetate.

Example 2

Figure 2:
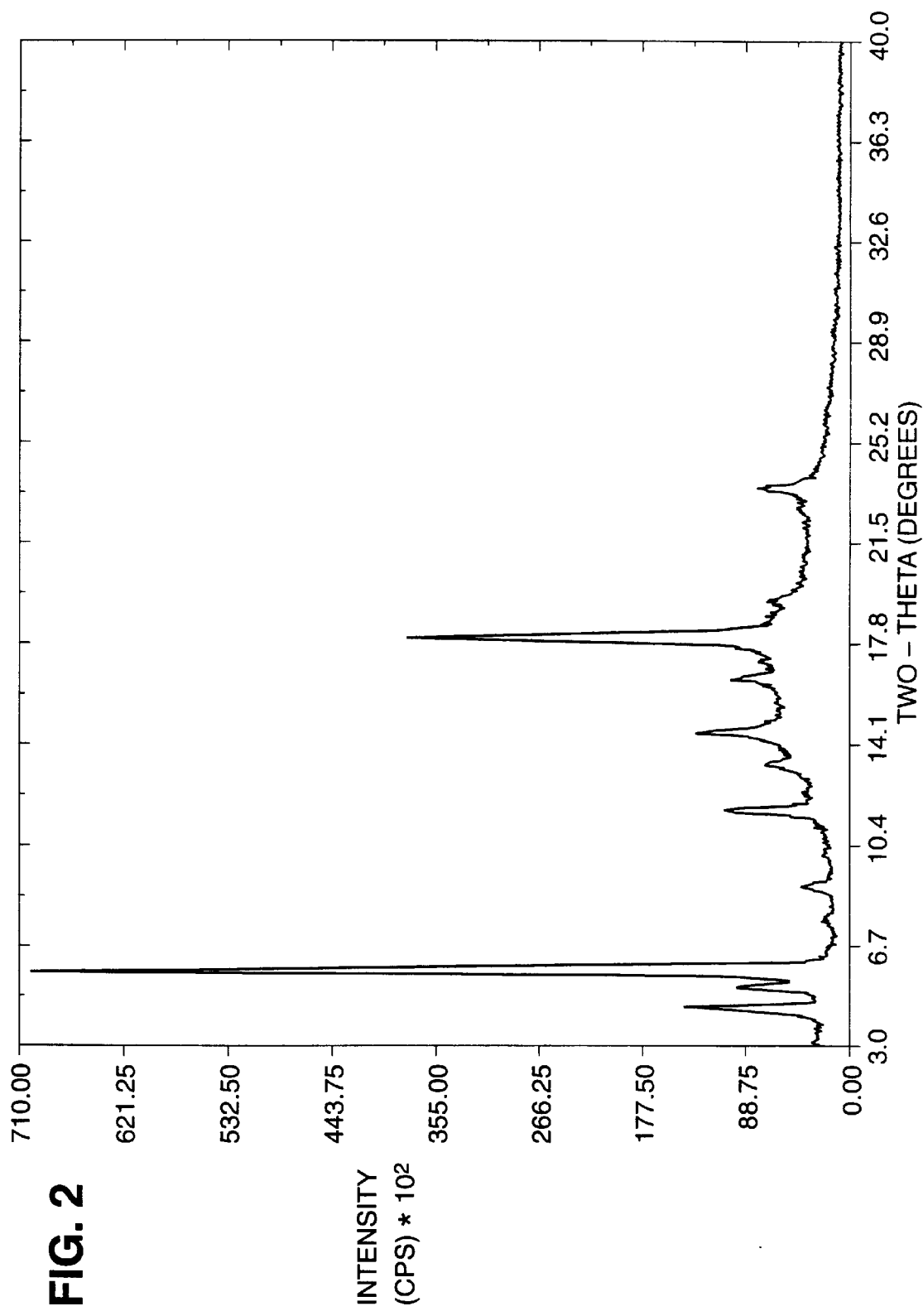
FIG. 2 illustrates an X-ray powder diffraction pattern of the second crystal form B of this invention.

Crystalline (3β,5α,25R)-3-[(β-D-4",6"-Bis[2-fluorophenyl carbamoyl]-cellobiosyl)oxy]-spirostan-12-one (3β,5α, 25R)-3-[(β-D-4",6"-Bis[2-fluorophenyl carbamoyl]-cellobiosyl)oxy]-spirostan-12-one (5 g) was dissolved in 50 ml. THF and 100 ml. ethanol at 30° C., and atmospherically distilled (i.e., at ambient pressure). When a final volume of 75 ml had been reached, the mixture was cooled to 0°–5° C., granulated for one hour, filtered and dried to afford 4.82 g of the title compound as a white to off-white solid form B that is thin flake with a doubly terminated blades habit. A representative X-ray diffraction pattern of this crystal (made substantially as described above) is depicted in FIG. 2.

In an analogous manner the product of Example 2 was prepared by substituting isopropanol for ethanol.

Preparation A1

(3β,5α,25R)-3-[(β-D-4",6"-Bis[2-fluorophenyl carbamoyl]-cellobiosyl)oxy]-spirostan-12-one

DEPROTECTION OF CHLOROACETATES

Sodium methoxide (250 mg) was added to a solution of (3β,5α,25R)-3-[(β-D-4",6"-Bis[2-fluorophenyl carbamoyl]-

2',2",3',3",6'-penta-chloroacetyl-cellobiosyl)oxy]-spirostan-12-one (25 g, 17.7 mmol) in THF (75 mL) and methanol (75 mL). After 20 min at room temperature, the reaction was quenched by the addition of acetic acid (0.5 mL). The solvent volume was reduced by one half in vacuo and an additional 75 mL of methanol was added. With vigorous stirring, the product was precipitated by the addition of water (75 mL). The solid was filtered, washed with 1:1 methanol:water and dried to afford 15 g of crude product. The product was purified by recrystallization from THF/cyclohexane/acetic acid (3:1:0.1). m.p. 272°–273° C. FAB MS: 1051 (M+Na)$^+$. Analysis calc. for $C_{53}H_{70}F_2N_2O_{16}+2H_2O$:C59.76; H 7.03; N 2.62. Found: C 59.91; H 7.32; N 2.61.

Preparation B1

(3β,5α,25R)-3-[(β-D-4",6"-Bis[2-fluorophenyl carbamoyl]-2', 2",3',3",6'-penta-chloroacetyl-cellobiosyl)oxy]-spirostan-12-one

CARBAMOYLATION USING CUPROUS CHLORIDE

Cuprous chloride (3.48 g, 36 mmol) was added to a solution of (3β,5α,25R)-3-[(β-D-2', 2", 3',3",6"-penta-chloroacetyl-cellobiosyl)oxy]-spirostan-12-one (10.0 9, 8.8 mmol) and 2-fluorophenylisocyanate (4 mL, 36 mmol) in dry dimethyl formamide (60mL) at room temperature. After 3 hours, the mixture was diluted with ethyl acetate (100 mL) and washed with 1N HCl(2×) and brine (1×), dried ($Na_2SO_4$), filtered and concentrated in vacuo. The residue was dissolved in methylene chloride (50 mL) and methanol (75 mL) was added. The methylene chloride was removed in vacuo and a solid precipitated from the methanol. The solid was filtered, washed with methanol and dried to afford 10.6 g product as a colorless solid (86%). m.p. 212°–214° C. FAB MS: 1433 (M+Na)$^+$. $^1$H NMR (250 MHz, CDCl$_3$)δ7.9 (m, 2 H); 7.05 (m, 8 H); 5.35 (dd, 1 H, J=8.0, 7.0 Hz); 5.28 (dd, 1 H, J=9.0, 8.0 Hz); 5.15 (dd, 1 H, J=9.0, 9.0 Hz); 5.05 (dd, 1 H, J=9.0, 8.0 Hz); 4.98 (dd, 1 H, J=8.0, 7.0 Hz); 4.72 (d, 1 H, J=9.0 Hz); 4.6 (m, 3 H); 4.4–3.4 (m, 18 H); 3.35 (dd, 1 H, J=10.0, 9.0 Hz); 2.5 (dd, 1 H, J=8.0, 7.0 Hz); 2.35 (dd, 1 H, J=13.0, 12.0 Hz); 2.1 (m, 1 H); 2.1–1.1 (m, 22 H); 1.05 (d, 3 H, J=7.0 Hz); 1.02 (s, 3 H); 0.85 (s, 3 H); 0.77 (d, 3 H, J=7.0 Hz).

Preparation C1

(3β, 5α, 25R)-3-[(β-D-2',2",3',3",6'-penta-chloroacetyl-cellobiosyl)oxy]-spirostan-12-one

PARAMETHOXY BENZYUDENE HYDROLYSIS

Trifluoroacetic acid (19 mL) was added to a solution of (3β, 5α,25R)-3-[(β-D-4",6"-O-[4-methoxybenzylidene]-2', 2",3',3",6'-penta-chloro-acetylcellobiosyl)oxy]-spirostan-12-one (23.7 9, 0.019 mol) in dichloromethane (150 mL) and methanol (50 mL). After 4 hours, the mixture was washed with water (3×), NaHCO$_3$ (2×) and brine (1×), dried (Na$_2$SO$_4$), filtered and concentrated. The residue was dissolved in a minimal amount of ethyl acetate and precipitated with hexanes. The solid was filtered and washed with hexanes and dried to afford 19.2 g product as a colorless solid (90%). m.p. 224°–226° C. FAB MS: 1159 (M+Na)$^{+\ 1}$H NMR (250 MHz, CDCl$_3$) δ5.2 (dd, 1 H, J=9.0, 9.0 Hz); 5.1 (dd, 1 H, J=9.0, 9.0 Hi); 4.95 (m, 2 H); 4.6 (m, 3 H); 4.2–3.4 (m, 21 H); 3.35 (dd, 1 H, J=9.0, 9.0 Hz); 3.1 (bs, 1 H); 2.5 (dd, 1 H, J=8.0, 7.0 Hz); 2.35 (dd, 1 H, J=13.0, 12.0 Hz); 2.1 (m, 1 H); 1.9–1.1 (m, 22 H); 1.05 (d, 3 H, J=7.0 Hz); 1.02 (s, 3 H); 0.85 (s, 3 H); 0.77 (d, 3 H, J=7.0 Hz).

Preparation D1

(3β,5α,25R)3[(β-D-4",6"-O-[4-methoxybenzyidene]-2', 2",3',3",6'-penta-chloro-acetylcellobiosyl)oxy]-spirostan-12-one

PARAMETHOXYBENZYUDENE FORMATION AND CHLOROACETYLATION

Camphorsulfonic acid (3 g) was added to a mixture of (3δ,5α, 25R)-3-[(β-D-cellobiosyl)oxy]-spirostan-12-one (50 g, 0.066 mol) and anisaldehyde dimethyl acetal (50 mL, 0.29 mol) in 1,2-dichloroethane (1500 mL). The suspension was heated to reflux temperature and 200 mL of solvent was distilled off. After 4 hours at reflux temperature, the gelatinous mixture was cooled to 0° C. and treated with pyridine (160 mL, 1.99 mol) and chloroacetic anhydride (170 g, 1 mmol). The reaction was allowed to warm to room temperature and after 2 hours, the mixture was washed with 1N HCl(3 ×), NaHCO$_3$ (1×) and brine (1×), dried (Na$_2$SO$_4$), filtered and concentrated in vacuo. The residue was dissolved in a minimum amount of ethyl acetate and the product was precipitated with hexanes. The solid was filtered, washed with hexanes and dried to afford 78.7 g product as a colorless solid (95%). m.p. 249°–251 ° C. FAB MS: 1277 (M+Na)$^+$. $^1$H NMR (250 MHz, CDCl$_3$) δ7.35 (d, 2 H, J=9.0 Hz); 6.88 (d, 2 H, J=9.0 Hz); 5.45 (s, 1 H); 5.3 (m, 2 H); 5.0 (m, 2 H); 4.7 (d, 1 H, J=7.0 Hz); 4.6 (m, 2 H); 4.3 (m, 2 H); 4.2 (dd, 1 H, J =11.0, 6.0 Hz); 4.2–3.5 (m, 14 H); 3.8 (s, 3 H); 3.35 (dd, 1 H, J=11.0, 10.0 Hz); 2.5 (dd, 1 H, J=8.0, 7.0 Hz); 2.35 (dd, 1 H, J=13.0, 12.0 Hz); 2.1 (m, 1 H); 2.1–1.0 (m, 25 H); 1.05 (d, 3 H, J=7.0 Hz); 1.02 (s, 3 H); 0.85 (s, 3 H); 0.77 (d, 3 H, J=7.0 Hz).

Preparation E1

(3β,5α,25R)-3-[(β-D-cellobiosyl)oxy]-spirostan-12-one

DEACYLATION

Sodium methoxide (50 mg) was added to a solution of (3β,5α,25R)-3-[(heptaacetyl-β-D-cellobiosyl)oxy]-spirostan-12-one (5 g, 4.77 mmol) in THF (75 mL) and methanol (25 mL). The solution was heated to a gentle reflux for 1 h. The mixture was cooled, and concentrated to 25 mL. Methanol (10 mL) and water (10 mL) were added and the precipitate was collected by vacuum filtration and washed with 1:1 methanol:water. The product was dried in a vacuum oven (80° C.) to afford 2.9 g (80%) of the title compound as a colorless solid. m.p. >250° C. FAB MS: 755 (M+H)$^+$. Analysis calc. for $C_{39}H_{52}O_{14}+2 H_2O$: C 59.22; H 8.41. Found: C 59.54; H 8.64.

Preparation F1

(3β,5α,25R)-3-[(heptaacetyl-β-D-cellobiosyl)oxy]-spirostan-12-one

ZINC FLUORIDE PROMOTED GLYCOSIDATION

A suspension of (3β,5α,25R)-3-hydroxy-spirostan-12-one (3.0 g, 6.97 mmol) and anhydrous zinc fluoride (2.88g, 27.9 mmol) in dry acetonitrile (175 mL) was dried by removal of 75 mL of acetonitrile by distillation. The suspension was allowed to cool, heptaacetyl-β-D-cellobiosyl bromide (9.75 g, 13.9 mmol) was added and the resulting suspension was heated to 65° C. for 3 hours. After cooling to room temperature, methylene chloride (150 mL) was added, stirred for 10 minutes and filtered. The filtrate was concentrated in vacuo to give 10 g of crude product. This material was dissolved in 8:2 chloroforn:methanol, preabsorbed on silica gel and purified by flash chromatography (eluant: 1:1 ethyl acetate hexanes) to give 6.81 g (93%) of the title compound. m.p. 220°–221° C. FAB MS: 1049 (M+H)$^+$. Analysis calc. for $C_{53}H_{76}O_{21}$+0.5 $H_2O$: C 60.11; H 7.34. Found: C 59.90; H 7.24.

It should be understood that the invention is not limited to the particular embodiments shown and described herein, but that various changes and modifications may be made without departing from the spirit and scope of this novel concept as defined by the following claims.

We claim:

1. A crystalline spirostanyl glycoside consisting of Form A or Form B of:

(3β,5α,25R)-3-((β-D-4",6"-bis-(2-fluorophenylcarbamoyl) cellobiosyl)oxy)-spirostan-12-one wherein Form A and Form B have the following X-ray diffraction d-spacings:

| Form A d-spacing of 20 largest peaks | | Form B d-spacing of 12 largest peaks |
|---|---|---|
| 21.10 | or | 19.96 |
| 17.46 | | 17.11 |
| 13.58 | | 15.14 |
| 10.49 | | 9.97 |
| 6.98 | | 7.57 |
| 6.78 | | 6.62 |
| 6.60 | | 6.09 |
| 6.34 | | 5.36 |
| 5.77 | | 5.15 |
| 5.52 | | 4.90 |
| 5.35 | | 4.57 |
| 5.12 | | 3.77 |
| 4.82 | | |
| 4.53 | | |
| 4.37 | | |
| 4.12 | | |
| 3.82 | | |
| 3.55 | | |
| 3.44 | | |
| 3.37. | | |

2. The crystalline spirostanyl glycoside of Form A as recited in claim 1 having the following X-ray diffraction d-spacing:

| Form A d-spacing of 20 largest peaks |
|---|
| 21.10 |
| 17.46 |
| 13.58 |
| 10.49 |
| 6.98 |
| 6.78 |
| 6.60 |
| 6.34 |
| 5.77 |
| 5.52 |
| 5.35 |
| 5.12 |
| 4.82 |
| 4.53 |
| 4.37 |
| 4.12 |
| 3.82 |
| 3.55 |
| 3.44 |
| 3.37 |

3. The crystalline spirostanyl glycoside as recited in claim 2 wherein Form A has the diffraction pattern of FIG. 1.

4. The crystalline spirostanyl glycoside of Form B as recited in claim 1 having the following X-ray diffraction d-spacing:

| Form B d-spacing of 12 largest peaks |
|---|
| 19.96 |
| 17.11 |
| 15.14 |
| 9.97 |
| 7.57 |
| 6.62 |
| 6.09 |
| 5.36 |
| 5.15 |
| 4.90 |
| 4.57 |
| 3.77 |

5. The crystalline spirostanyl glycoside as recited in claim 4 wherein form B has the X-ray diffraction pattern of FIG. 2.

6. A pharmaceutical composition for the treatment of hypercholesterolemia or atherosclerosis in a mammal which comprises a pharmaceutically effective amount of a crystalline spirostanyl glycoside according to claim 1 and a pharmaceutically acceptable carrier.

7. A method for treating hypercholesterolemia or atherosclerosis in a mammal comprising administering to a mammal suffering from hypercholesterolemia or atherosclerosis a pharmaceutically effective amount of a crystalline spirostanyl glycoside according to claim 1.

8. A process for preparing a crystalline steroidal glycoside comprising: mixing (3β,5α,25R)-3-[(β-D-4",6"-bis-[2-fluorophenylcarbamoyl]cellobiosyl)oxy]-spirostan-12-one in ethyl acetate or acetonitrile and allowing crystalline (3β,5α,25R)-3-[(β-D-4",6"-bis-[2-fluorophenylcarbamoyl] cellobiosyl)oxy]-spirostan-12-one to form.

9. The process as recited in claim 8 wherein the ethyl acetate or acetonitrile solution is heated and upon cooling crystals form.

10. A process for preparing a crystalline steroidal glycoside comprising: mixing (3β,5α,25R)-3-[(β-D-4",6"-bis-[2-fluorophenylcarbamoyl]cellobiosyl)oxy]-spirostan-12-one in an alkanol($C_{1-C4}$) optionally with up to 70% water and allowing crystalline (3β,5α,25R)-3-[(β-D-4",6"-bis-[2-fluorophenylcarbamoyl]cellobiosyl)oxy]-spirostan-12-one to form.

11. The process as recited in claim 10 wherein the solvent is ethanol, isopropanol or n-propanol(30 to 70%)/water(70 to 30%) and the solution is heated, and upon cooling crystals form.

* * * * *